ated Patent [19]
Shepherd et al.

[11] 3,951,742
[45] Apr. 20, 1976

[54] PRODUCTION OF ZEAXANTHIN
[75] Inventors: David Shepherd, Morges; Jaroslav Dasek, Yverdon, both of Switzerland
[73] Assignee: Societe d'Assistance Technique pour Produits Nestle S.A., Lausanne, Switzerland
[22] Filed: July 18, 1974
[21] Appl. No.: 489,473

[30] Foreign Application Priority Data
July 26, 1973  Switzerland...................... 10903/73

[52] U.S. Cl................................. 195/28 R; 195/96
[51] Int. Cl.².......................................... C12D 13/02
[58] Field of Search...................... 195/28 R, 96, 29

[56] References Cited
FOREIGN PATENTS OR APPLICATIONS
2,138,000  2/1972  Germany
OTHER PUBLICATIONS
Chemical Abstracts, Vol. 70, 139061h, 1972.

Primary Examiner—Alvin E. Janenholtz
Attorney, Agent, or Firm—Watson Leavenworth Kelton & Taggart

[57] ABSTRACT

A process for the preparation of zeaxanthin which comprises culturing a microorganism of the genus Flavobacter producing this pigment, in a nutrient medium containing at least one carbohydrate as assimilable carbon source, at least one source of assimilable amino nitrogen containing free amino acids, mineral salts, oligoelements and vitamins, the spectrum of amino acids of the medium being modified by increasing the content in the medium of at least one of the sulphur-containing amino acids methionine, cystine and cysteine, in relation to the content in the medium of other amino acids, whilst limiting the quantity of the sulphur-containing amino acid added to the medium to a value not exceeding 1 mg/ml, and continuing culturing until a substantial quantity of intracellular zeaxanthin has been obtained.

6 Claims, No Drawings

PRODUCTION OF ZEAXANTHIN

This invention relates to a process for the preparation of zeaxanthin by culturing a microorganism of the genus Flavobacter producing this pigment. More particularly the microorganism is cultured in a nutrient medium containing at least one carbohydrate as assimilable carbon source, at least one source of assimilable amino nitrogen containing free amino acids, and mineral salts, oligoelements and vitamins.

The yellow pigment known as zeaxanthin or 3,3′-dihydroxy-$\beta$-carotene can be used, for example, as an additive in poultry feeds to strengthen the yellow colour of the skin of animals of this kind or to accentuate the colour of the yolk of their eggs. This compound is also suitable for use as a colorant, for example in the cosmetics industry and in the food industry.

The synthesis of pigments by certain microorganisms, in particular the synthesis of carotenoid pigments by bacteria of the genus Flavobacter, is a known phenomenon. However, the industrial preparation of pigments of this kind by biosynthesis has generally proved to be difficult and, because they are often very poor, the yields obtained necessitate the use of very large quantities of culture media if appreciable quantities of pigment are to be obtained.

It is also known that mineral salts, oligoelements and vitamins or other substances which promote the growth of microorganisms and the formation of products of their metabolism, can be added to the culture medium. However, so far as the production of zeaxanthin is concerned, even the use of the richest culture media does not produce zeaxanthin in a quantity sufficient to justify manufacture on a commercial scale.

The object of the present invention is to provide a process for preparing zeaxanthin by biosynthesis which enables the yield in which this pigment is obtained to be considerably increased without any appreciable increase in the cost of the operation.

The present invention provides a process for the preparation of zeaxanthin which comprises culturing a microorganism of the genus Flavobacter producing this pigment, in a nutrient medium containing at least one carbohydrate as assimilable carbon source, at least one source of assimilable amino nitrogen containing free amino acids, mineral salts, oligoelements and vitamins, the spectrum of amino acids of the medium being modified by increasing the content in the medium of at least one of the sulphur-containing amino acids, methionine, cystine and cysteine, in relation to the content in the medium of other amino acids, whilst limiting the quantity of methionine and/or cystine and/or cysteine added to the medium to a value not exceeding 1 mg/ml, and continuing culturing until a substantial quantity of intracellular zeaxanthin has been obtained.

The process according to the invention makes it possible to obtain increased outputs in relation to those obtained by conventional processes. The increase in output obtained by the process according to the invention over that of conventional processes can amount, for example, to a factor of as high as four depending upon the particular embodiment. The increase in yield is of course reflected in a considerable reduction in production costs.

In the practical application of the process according to the invention, the source of assimilable carbon can be glucose or saccharose used in a proportion of from 0.1 to 15 percent by weight of the culture medium, whilst the source of assimilable amino nitrogen can be a yeast extract and/or a corn steep liquor and/or a protein hydrolysate used in a proportion of from 0.1 to 8 percent by weight of the medium. Magnesium sulphate can also be included in this medium in a proportion of from 0.1 to 2 percent by weight. All the aforementioned substances are diluted in tap water, for example, which makes up the balance to 100 percent by weight.

The spectrum of amino acids of the medium can be modified by adding methionine and/or cystine and/or cysteine in a given quantity in L- and/or D- and/or DL-form. The methionine and/or cystine and/or cysteine content of the medium is preferably adjusted to from 3 to 10 percent of the content of other amino acids in the medium.

An inoculum of a microorganism of the genus Flavobacter which produces zeaxanthin can then be added to the nutrient solution thus prepared. In the context of the invention, a microorganism of the genus Flavobacter is a microorganism selected from bacteria of this kind and mutants of such microorganisms. The fermentation process can take place with agitation and aeration, at suitable pH-values and temperatures and over the period of time required to produce an appreciable quantity of intracellular zeaxanthin. Thereafter the culture may be dried optionally after concentration. Zeaxanthin may be extracted from the cells with a polar organic solvent such as acetone, ethyl alcohol or a chlorine-containing solvent such as chloroform. Alternatively, the biomass after separation from the culture medium, by centrifugation, decantation or filtration, may be used as such, for example, as an additive in poultry feeds.

It has been found that the concentration of zeaxanthin in the biomass thus obtained is distinctly higher (an increase of approximately 50 percent) than the concentration obtained by growing the same microorganism in a conventional nutrient medium. It has also been found that this increase is not governed by the absolute quantity of methionine and/or cystine and/or cysteine added to the starting nutrient solution, but by its relative quantity in relation to the quantity of amino acids present in the starting nutrient solution or culture medium.

However, an inhibiting effect is observed when the content in the medium of sulphur-containing amino acids is increased to an excessive level, and it is for this reason that the quantity of methionine and/or cystine and/or cysteine added to the medium is limited to a value which does not exceed 1 mg/ml.

It is worth noting here that a phenomenon similar to the remarkable effect mentioned above has been observed in the case of an addition to the starting nutrient solution of at least one of the bivalent metal ions $Fe^{++}$, $Co^{++}$, $Mn^{++}$ and $Mo^{++}$ without the addition of at least one of the aforementioned sulphur-containing amino acids, this phenomenon being reflected by an increase in the concentration of zeaxanthin in the biomass of as much as 50 percent, and by an increase in the biomass of again as much as 50 percent i.e. by double the output of zeaxanthin in relation to that obtained by growing the same microorganism in a conventional nutrient medium.

In one embodiment of the process according to the invention, the spectrum of oligoelements in the medium is modified by the addition of at least one of the bivalent metal ions $Fe^{++}$ and/or $Co^{++}$ and/or $Mn^{++}$ and/or $Mo^{++}$ ions added to the medium to a level not exceeding 0.2 M in order to avoid an inhibiting effect. The aforementioned metal ions are preferably added in a quantity of from 0.0005 to 0.1 M and it is of particular advantage to add them in a quantity of from 0.001 to 0.05 M. The aforementioned metal ions can be added in the form of soluble salts such as, for example, ferrous sulphate or ferrous chloride, cobalt, chloride, sodium molybdate or manganese sulphate. The amino acid preferably added is methionine and the metal ion preferably added is $Fe^{++}$.

It has been found that a synergistic effect is obtained by the simultaneous addition of at least one of the aforementioned sulphur-containing amino acids and at least one of the aforementioned metal ions. In this case, the output of zeaxanthin can reach as much as four times the output obtained by growing the same microorganism in a conventional nutrient solution. That part of the increase in output due to an increase in the concentration of zeaxanthin in the biomass is almost twice that part due to the increase of the biomass itself.

The process according to the invention is illustrated by the following Examples:

EXAMPLE 1

A culture medium with the following composition is prepared:

| | |
|---|---|
| Glucose | 3% |
| Casein hydrolysate (tryptone) | 1% |
| Yeast extract | 1% |
| Magnesium sulphate | 0.5% |
| Tap water balance to | 100% |

This medium is poured into bottles, subsequently sterilised for 20 minutes at 120°C and then cooled to 25°C. The pH-value of the medium after sterilisation is 7.3. An inoculum of a mutant of the strain ATCC No. 21588 of the genus Flavobacter, obtained as described in German Pat. Specification No. 2252364, is then introduced into the medium. Culturing of this microorganism in the said medium is continued for 48 hours at a temperature of 25°C, the medium being permanently aerated by agitation of the bottles in rotary agitators turning at 200 rpm. The bottles are then centrifuged and the cellular mass collected, representing 10.5 g of dry material per liter of culture broth.

The quantity of zeaxanthin present in the cells is determined by extraction of the pigment, followed by measurement of the optical density of the extract. In order to obtain the extract, a suspension of cells is prepared in 5 ml of saline, an equal volume of acetone is then added, the mixture is shaken for a few minutes and, finally, subjected to filtration. The optical density of the filtrate is measured in a spectrophotometer at 450 nm. The quantity of zeaxanthin is determined by comparison of the optical density measured with a standard curve obtained by measuring the optical density of several solutions containing different quantities of pure zeaxanthin.

The same process of extraction and measurement is applied to several samples of the same culture. The arithmetic mean of the numerical results obtained is formed. The quantity of zeaxanthin present in the cells or specific concentration thus determined increases to 5.16 mg per g of cellular mass, which represents an output of zeaxanthin of 54.2 $\mu$g per ml of culture broth. These values are accurate to $\pm$ 3–5 percent.

The Examples which follow are given in the form of a Table. The substance added to the culture medium and the quantity added can be found in the column headed "type of treatment." This quantity is expressed in g of amino acid in question per liter of medium and in molar concentration of ion in question in the medium. The column headed "zeaxanthin" indicates the quantity of zeaxanthin obtained in $\mu$g per ml of culture broth. The column headed "cellular mass" shows the quantity of dry material produced in g per liter of broth. The column headed "specific concentration" expresses the quantity of zeaxanthin present in the cells produced in mg of zeaxanthin per g of dry material.

In each case, the operations are carried out in the same way as described in Example 1. The operation in which sulphurcontaining amino acid and/or bivalent metallic ion is/are added to the medium takes place just before the operation by which the inoculum is introduced or before the operation by which the medium is sterilised. The numerical values relating to the output of cellular mass and of zeaxanthin are given with the same accuracy as indicated in Example 1, i.e. $\pm$ 3–5 percent. They represent arithmetic means formed from the results obtained with 3 to 6 samples of one and the same culture.

The starting medium and the type of inoculum used were varied in the last Examples in order to demonstrate that the success of the process is not dependent upon a particular composition of the medium or upon the performances of a single mutant. Thus, in Example 20, the starting medium contains 2 percent of yeast extract and 1 percent of tryptone, whilst in Example 21 the starting medium contains 1 percent of yeast extract and 2 percent of tryptone.

| Example No. | Type of treatment additive(s) | quantity g/l | M | Zeaxanthin µg/ml | Cellular mass g/l | Specific concentration mg/g |
|---|---|---|---|---|---|---|
| 1 | none | | | 54.2 | 10.5 | 5.16 |
| 2 | methionine | 0.06 | | 65.8 | 10.7 | 6.14 |
| 3 | methionine | 0.12 | | 77.0 | 8.3 | 9.27 |
| 4 | methionine | 0.24 | | 72.0 | 7.6 | 9.47 |
| 5 | methionine | 0.48 | | 50.3 | 6.1 | 8.24 |
| 6 | cystine | 0.12 | | 71.4 | 11.5 | 6.2 |
| 7 | cysteine | 0.12 | | 73.0 | 10.8 | 6.75 |
| 8 | $Fe^{++}$ | | 0.002 | 118.8 | 14.5 | 8.19 |
| 9 | $Fe^{++}$ | | 0.01 | 124.4 | 13.8 | 9.01 |
| 10 | $Co^{++}$ | | 0.001 | 91.4 | 9.9 | 9.23 |
| 11 | $Mo^{++}$ | | 0.002 | 88.0 | 10.5 | 8.38 |
| 12 | $Mn^{++}$ | | 0.002 | 86.0 | 11.6 | 7.41 |
| 13 | methionine $Fe^{++}$ | 0.12 | 0.002 | 168 | 11.6 | 14.48 |
| 14 | methionine $Fe^{++}$ | 0.12 | 0.01 | 188 | 9.6 | 19.5 |

-continued

| Example No. | Type of additive(s) | treatment quantity g/l | M | Zeaxanthin μg/ml | Cellular mass g/l | Specific concentration mg/g |
|---|---|---|---|---|---|---|
| 15 | cysteine Fe$^{++}$ | 0.12 | 0.002 | 151.4 | 13.9 | 10.8 |
| 16 | cystine Fe$^{++}$ | 0.12 | 0.002 | 143.2 | 14.0 | 10.3 |
| 17 | methionine Mn$^{++}$ | 0.12 | 0.002 | 146.4 | 14.8 | 9.8 |
| 18 | methionine Co$^{++}$ | 0.12 | 0.001 | 131.1 | 11.6 | 11.3 |
| 19 | cystine Mn$^{++}$ | 0.12 | 0.002 | 134.6 | 12.6 | 10.6 |
| 20 | methionine Fe$^{++}$ | 0.12 | 0.002 | 156.4 | 13.4 | 11.67 |
| 21 | methionine Fe$^{++}$ | 0.12 | 0.002 | 165.0 | 13.2 | 12.5 |
| 22 | methionine Fe$^{++}$ | 0.12 | 0.002 | 168.0 | 12.7 | 13.2 |

We claim:

1. In a process for the preparation of zeaxanthin pigment which comprises culturing a microorganism of the genus Flavobacter producing this pigment, in a nutrient medium containing at least one carbohydrate as assimilable carbon source, at least one source of assimilable amino nitrogen containing free amino acids, mineral salts, oligoelements and vitamins to produce intracellular zeaxanthin, the improvement which comprises modifying the spectrum of amino acids of the medium to enhance the production of said zeaxanthin by adding at least one of the sulphur-containing amino acids methionine, cystine and cysteine thereto, the quantity of added sulphur-containing amino acid not exceeding 1 μg/ml, but being sufficient to adjust the sulphur-containing amino acid content of said medium to from 3 to 10 percent of the content of other amino acids in said medium.

2. A process as claimed in claim 1, wherein the carbohydrate is glucose or sucrose used in a proportion of from 0.1 to 15 percent by weight of the medium, and the amino acids are in the form of yeast extract and/or corn steep liquor and/or protein hydrolysate used in a proportion of from 0.1 to 8 percent by weight of the medium.

3. A process as claimed in claim 1, wherein the medium contains magnesium sulphate in a proportion of from 0.1 to 2 percent by weight.

4. A process as claimed in claim 1, wherein at least one of the bivalent metal ions Fe$^{++}$, Co$^{++}$, Mo$^{++}$, Mn$^{++}$, is added to the medium at a concentration not exceeding 0.2M.

5. A process as claimed in claim 4, wherein the concentration of the bivalent metal ion or ions added is from 0.0005 to 0.1 M.

6. A process as claimed in claim 5, wherein the concentration of metal ion or ions added is from 0.001 to 0.05 M.

* * * * *